United States Patent
King et al.

(10) Patent No.: US 6,236,747 B1
(45) Date of Patent: May 22, 2001

(54) SYSTEM AND METHOD FOR IMAGE SUBTRACTION FOR BALL AND BUMPED GRID ARRAY INSPECTION

(75) Inventors: Steven Joseph King, Merrimack, NH (US); Jonathan Edmund Ludlow, Lexington, MA (US)

(73) Assignee: Acuity Imaging, LLC, Nashua, NH (US)

( * ) Notice: Subject to any disclaimer, the term of this patent is extended or adjusted under 35 U.S.C. 154(b) by 0 days.

(21) Appl. No.: 09/134,654

(22) Filed: Aug. 14, 1998

Related U.S. Application Data

(63) Continuation-in-part of application No. 08/824,173, filed on Mar. 26, 1997, now Pat. No. 5,926,557, which is a continuation-in-part of application No. 08/807,397, filed on Feb. 26, 1997, now Pat. No. 5,943,125.

(51) Int. Cl.$^7$ .............................. G06K 9/00; H04N 7/18; G01N 21/00
(52) U.S. Cl. ....................... 382/149; 382/145; 382/147; 348/92; 356/237.1
(58) Field of Search ..................................... 382/149, 150, 382/145, 219, 142, 146, 147; 348/86, 92; 356/237.1, 239.3, 239.5

(56) References Cited

U.S. PATENT DOCUMENTS

| | | | |
|---|---|---|---|
| 4,028,728 | 6/1977 | Sharp | 358/106 |
| 4,677,473 | 6/1987 | Okamoto et al. | 358/101 |
| 4,688,935 | 8/1987 | Barnes et al. | 356/36 |
| 4,688,939 | 8/1987 | Ray | 356/237 |
| 4,695,157 | 9/1987 | Schoenbaum et al. | 356/237 |
| 4,697,076 | 9/1987 | Yoshida | 250/223 B |
| 4,782,238 | * 11/1988 | Radl et al. | 250/559.36 |
| 4,972,093 | 11/1990 | Cochran et al. | 250/572 |
| 4,988,202 | 1/1991 | Nayar et al. | 356/394 |

(List continued on next page.)

Primary Examiner—Leo Boudreau
Assistant Examiner—Daniel G. Mariam
(74) Attorney, Agent, or Firm—Bourque & Associates, P.A.

(57) ABSTRACT

An inspection system and method uses a first illumination apparatus, such as a ring illumination apparatus to illuminate one or more reflective elements, such as solder balls on an electronic component or other protruding surfaces or objects. The ring illumination apparatus includes a substantially ring-shaped light source that provides a substantially even illumination across the one or more reflective elements. An illumination detection device detects light beams reflecting off of the illuminated reflective elements for forming a first captured image. The system and method then uses a second, different illumination apparatus, such as an on-axis illumination apparatus to illuminate the reflective elements. The second illumination apparatus is selected so as to illuminate unwanted reflective elements substantially the same as they are illuminated by the first illumination apparatus while illuminating the desired reflective elements differently. A second image of the object is then captured by the illumination detection device. The second image is then subtracted from the first or vice-versa by an image processor to generate a resulting image that is substantially devoid of the unwanted reflective elements, yet including the desired reflective elements, which are further analyzed using additional image analyzed techniques.

17 Claims, 16 Drawing Sheets

U.S. PATENT DOCUMENTS

| | | | |
|---|---|---|---|
| 5,023,916 | 6/1991 | Breu | 382/150 |
| 5,030,008 | 7/1991 | Scott et al. | 356/394 |
| 5,039,868 | 8/1991 | Kobayaski et al. | 250/572 |
| 5,051,872 | 9/1991 | Anderson | 362/32 |
| 5,058,178 | 10/1991 | Ray | 382/150 |
| 5,064,291 | 11/1991 | Reiser | 356/372 |
| 5,072,127 | 12/1991 | Cochran et al. | 250/572 |
| 5,097,516 | 3/1992 | Amir | 382/274 |
| 5,118,193 | 6/1992 | Brown et al. | 356/394 |
| 5,127,727 | 7/1992 | Arnold et al. | 356/237 |
| 5,137,362 | 8/1992 | LeBeau | 356/394 |
| 5,166,985 | 11/1992 | Takagi et al. | 382/150 |
| 5,245,671 | 9/1993 | Kobayashi et al. | 382/150 |
| 5,247,344 | 9/1993 | Doan | 356/394 |
| 5,257,714 | 11/1993 | Beers et al. | 228/6.2 |
| 5,267,217 | 11/1993 | Tokura et al. | 356/237 |
| 5,302,836 * | 4/1994 | Siu | 250/559.34 |
| 5,394,246 | 2/1995 | Sugawara | 356/394 |
| 5,406,372 | 4/1995 | Vodanovic et al. | 356/394 |
| 5,411,682 * | 5/1995 | Nagashima | 264/36.15 |
| 5,418,879 | 5/1995 | Kalnajs et al. | 385/115 |
| 5,420,689 | 5/1995 | Siu | 356/394 |
| 5,424,838 | 6/1995 | Siu | 356/394 |
| 5,440,391 * | 8/1995 | Smeyers et al. | 356/375 |
| 5,461,417 | 10/1995 | White et al. | 348/131 |
| 5,495,424 | 2/1996 | Tokura | 364/507 |
| 5,519,496 | 5/1996 | Borgert et al. | 356/394 |
| 5,533,146 | 7/1996 | Iwai | 382/150 |
| 5,539,485 * | 7/1996 | White | 396/431 |
| 5,574,801 | 11/1996 | Collet-Beillon | 382/150 |
| 5,581,632 | 12/1996 | Koljonen et al. | 382/150 |
| 5,598,345 | 1/1997 | Tokura | 364/489 |
| 5,604,550 | 2/1997 | White | 396/429 |
| 5,694,482 * | 12/1997 | Maali et al. | 382/151 |
| 5,729,894 * | 3/1998 | Roastoker et al. | 29/832 |
| 5,949,901 * | 9/1999 | Nichani et al. | 382/149 |

* cited by examiner

SYSTEM AND METHOD FOR IMAGE SUBTRACTION FOR BALL AND BUMPED GRID ARRAY INSPECTION

CROSS-REFERENCE TO RELATED APPLICATIONS

The present application is a Continuation-in-Part of U.S. patent application Ser. No. 08/824,173 filed Mar. 26, 1997, which is now U.S. Pat. No. 5,926,557 issued Jul. 20, 1999 entitled "INSPECTION METHOD", which is a Continuation-in-Part of U.S. patent application Ser. No. 08/807,397 filed Feb. 26, 1997, which is now U.S. Pat. No. 5,943,125 issued Aug. 24, 1999 entitled "INSPECTION SYSTEM" both of which are assigned to the assignee of the present invention.

FIELD OF THE INVENTION

The present invention relates to inspection systems and methods and, in particular, to a system and method for inspecting ball and bumped grid arrays utilizing multiple immumination apparatuses and image subtraction techniques to eliminate unwanted features from the image to be inspected.

BACKGROUND OF THE INVENTION

Digital data and signal processing techniques and technology have tremendously advanced the ability to use computers as data processing systems to accomplish sophisticated inspection procedures without human intervention. Almost every type of product can benefit from low cost, high precision, high speed inspection technology derived from these new digital data and signal processing techniques.

For example, in computers and other electronic systems, the electrical connections between electronic components ("chips") are critical to the operation of the system. As a result of recent technological advances, electronic components are decreasing in size and increasing in complexity, requiring a larger number of electrical connections to be made in a smaller area. Inspection of the electronic components during a manufacturing process helps assure that electrical contacts are properly formed and prevents failed electrical connections between electronic components.

Semiconductor chips, for example, must be physically and electronically connected to printed circuit boards using solder or flux between electrical contacts on the chip and the circuit board. One type of electrical contact includes metal areas or pads on the semiconductor chip that must be electrically connected to corresponding metal areas or pads on the printed circuit board. Typically, small deposits of solder and/or flux are placed on the pads, heated and re-flowed, establishing a mechanical and electrical connection between the corresponding pads.

A common soldering technique is to use preformed balls of solder that are placed on the metal pads on the chip or substrate of an electronic component, commonly known as a ball grid array (BGA). With the decrease in size of the electronic components and the increase in complexity, as many as 400 or more solder balls must be precisely positioned in a predefined pattern on the chip or substrate to electrically connect the chip to the printed circuit board. During the process of positioning and adhering the solder balls to the metal pads on the chip or substrate, a number of defects can occur that will detrimentally affect the electrical connection between the chip and the printed circuit board.

If a solder ball does not sufficiently adhere to one of the pads, a critical electrical connection between the chip and the printed circuit board could be lost. The misplacement of a solder ball can also result in a failed connection and/or an electrical short circuit with another adjacent solder ball or metal pad. A solder ball that is malformed, too large or too small could also result in a defective electrical connection even if properly positioned at the precise location on the pad.

Inspection of the solder balls is therefore critical to assure proper size and shape of the solder balls as well as precise placement and adherence of the solder balls to the appropriate pads on the printed circuit board prior to establishing connections between the electronic components. Inspection is also required for other electronic components requiring precise electrical connections.

One prior art method of inspection is to have a human operator visually inspect each chip, printed circuit board or other electronic component to detect defects in the solder balls or other electrical contacts. Manual inspection, however, is time-consuming, inaccurate, and a strain on human inspectors, particularly in light of the decreased size of the electronic components and increased number of connections.

Video systems have also been used to inspect solder balls or other contacts or features on electronic components. In such systems, a light, such as a ring light, illuminates the surface of the electronic component to be inspected. A camera detects the light reflected from the solder balls or contacts on the electronic component and the reflected image is displayed on a monitor.

The ring lights used in prior art inspection systems have been unable to provide adequate illumination of solder balls on an electronic component. One problem occurs when the ring lights do not provide light beams of sufficient intensity at outer regions of the area being inspected and thus fail to illuminate some of the solder balls being inspected, resulting in inaccurate determinations of the absence/presence or position of the solder balls. Another problem exists when a solder ball is only partially illuminated, preventing an accurate measurement of the true diameter and circularity of the solder ball.

Other inspection devices direct the light beams at a high angle with respect to the chip, causing the light beams to reflect off the metalized pads, the substrate surface, or other substantially flat reflective surfaces that are not being inspected. In the resulting illuminated image detected by the video camera, the solder balls are difficult to discern from the metal pads and other substantially flat reflective surfaces. This is a particular problem where the illuminated image is to be processed and analyzed by an image processor to detect the absence/presence of solder balls and the condition of solder balls (e.g. location, diameter, and circularity).

Other ring lights direct light parallel to the surface of the component being inspected and must be positioned against or around each electronic component to obtain sufficient illumination of the entire surface of the electronic component. If this type of ring light is not positioned against the surface of the component being inspected, the component will not be sufficiently illuminated, particularly at the edges of the component. This type of ring light must therefore be raised and lowered for each individual electronic component to adequately illuminate each electronic component and does not allow a large number of electronic components to be sequentially inspected quickly during a manufacturing process.

A further problem is that many prior art vision inspection systems still require a human operator to examine the illuminated image of the electronic component and detect defects such as missing, misplaced or malformed solder balls. A visual inspection of the illuminated image still does not enable an accurate measurement of the size and shape of the solder balls.

Accordingly, a need exists for a system and method for inspecting solder balls or other reflective objects, surfaces or elements that adequately illuminates all of the reflective elements being inspected, allowing accurate measurements and inspection of the reflective elements without illuminating other generally planar surfaces that are not being inspected. There is also a need for a system and method that quickly and accurately detects absence/presence of the illuminated reflective elements, determines their position, and measures the size and shape, e.g. the diameter and circularity of any protruding object, if desired.

SUMMARY OF THE INVENTION

The present invention features a system and method of inspecting an article having one or more deviations, such as protrusions or intrusions, from a generally planer surface of the article by capturing at least two images of the article with an image capture device. Each image is captured while the article is illuminated using a different illumination apparatus. The illumination apparatuses are selected such that features of interest on the article appear differently under the different illumination apparatuses while unwanted features appear substantially the same under both illumination apparatuses. The system, in addition to the illumination apparatuses and image capture device, includes an image processor, which subtracts the second captured imaged from the first captured image such that the unwanted features of the article are substantially eliminated.

The inspection method comprises: sequentially illuminating an article using first and second illumination apparatuses, said first and second illumination apparatuses selected to illuminate unwanted features on said article similarly and to illuminate desired features on said article differently; capturing a first image of the article with an image capture device while the article is illuminated by the first illumination apparatus; capturing a second image of the article with the image capture device while the article is illuminated with the second illumination apparatus; and processing the first and second images by subtracting the second image from the first image to produce a resulting image wherein the unwanted features are eliminated.

The preferred method is used to inspect an array of solder balls on an electronic component and, more specifically, for inspecting ball and bumped grid arrays to highlight the solder balls. By eliminating the unwanted features, an inspection system can more readily inspect information related to the features of interest, such as the solder balls, which preferably includes, but is not limited to, the absence/presence of each solder ball in the array of solder balls, the location of each solder ball, the pitch between solder balls, malformed solder balls, the diameter of each solder ball and the circularity of each ball.

In the preferred embodiment, which is especially suitable for inspecting ball and bumped grid arrays, the first illumination apparatus comprises a low angle ring illumination apparatus, such as the one more fully disclosed in commonly-owned co-pending patent application, Ser. No. 08/824,173, which is now U.S. Pat. No. 5,926,557, which is incorporated herein by reference. The second illumination apparatus preferably comprises an on-axis illumination apparatus, which is substantially co-linear with the image capture device.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENT

Figure 1:
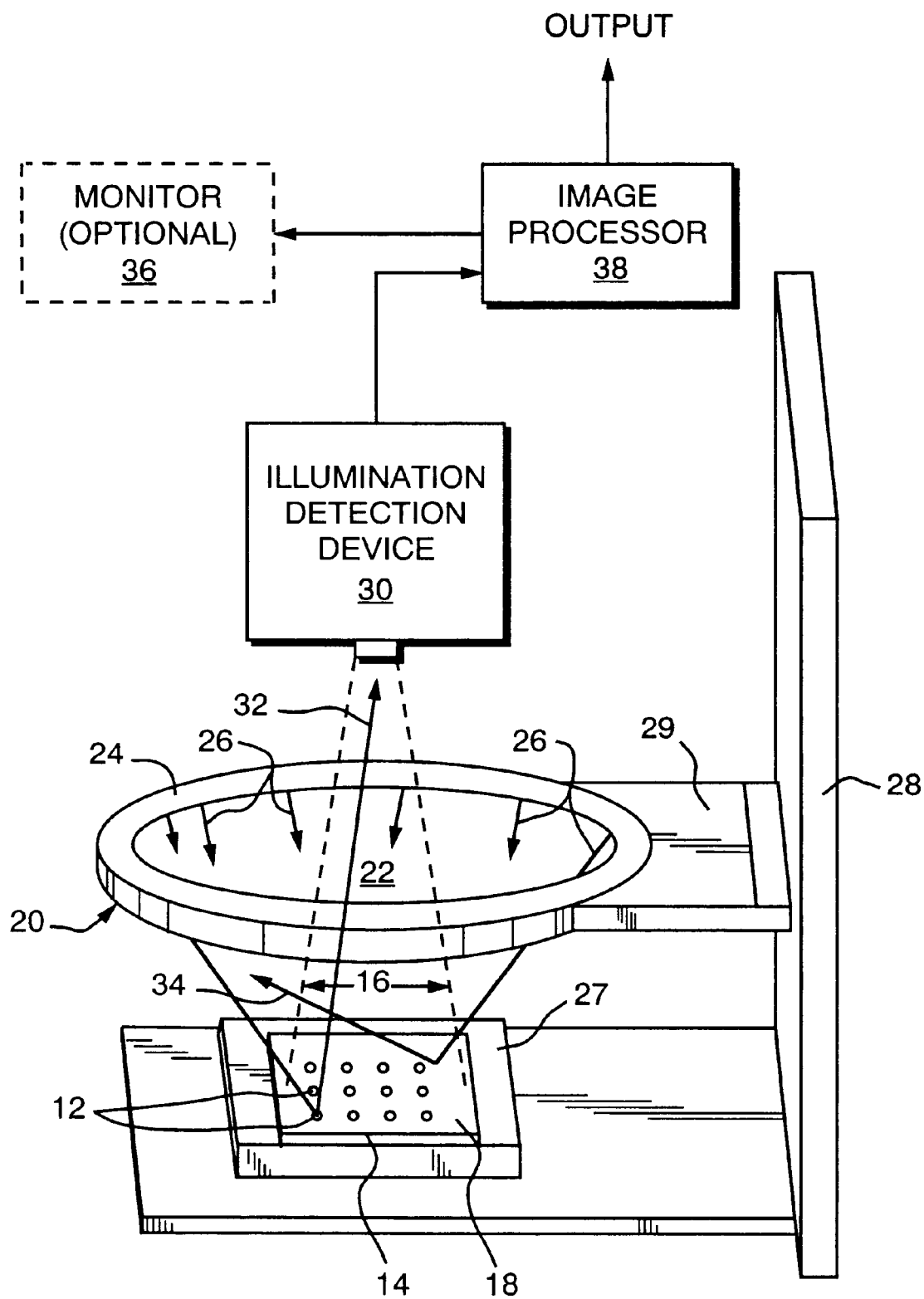
FIG. 1 is a schematic view of an inspection system for inspecting one or more surfaces or objects according to one embodiment of the present invention.

An inspection system 10, FIG. 1 (shown in an exaggerated perspective view for purposes of clarity), according to the present invention, is used to inspect one or more reflective elements, such as protruding reflective surfaces or objects 12, disposed on an article 14. In one example, the protruding reflective objects 12 are disposed on a generally planar surface 18 that has both reflective and non-reflective areas. The article 14 typically includes an array of protruding reflective objects 12 made of metal or other light reflective materials.

In the exemplary embodiment, the inspection system 10 is used to inspect an array of solder balls disposed on metal pads on a chip or other substrate of an electronic component, such as BGA or micro BGA semi-conductor packages, chip scale packaging (CSP), or flex circuits. The positioning, size and shape of solder balls are inspected to facilitate proper electrical connection between the chip and other electronic components, such as printed circuit boards. The present invention, however, contemplates inspecting any type or shape of reflective elements including, but not limited to, protrusions, deviations, and other contoured surfaces or objects on an article, arranged in any pattern on any type of article.

The present inspection system 10 includes a field of view 16 that covers the protruding reflective objects 12 disposed on the article 14, and a ring illumination apparatus 20 defining an aperture 22 through which the field of view 16 extends. The ring illumination apparatus 20 includes a substantially ring-shaped light source 24 that generates light beams 26 and directs the light beams 26 into the field of view 16 on the article 14 such that the protruding reflective objects 12 are illuminated. The light beams 26 preferably provide a substantially even intensity of light across the field of view 16 on the article 14 and a substantially even illumination of all of the protruding reflective objects 12 in the field of view 16, as will be described in greater detail below. Although shown as a generally circular ring light, ring illumination apparatus 20 may also be in the shape of an oval or other similar shape.

The inspection system 10 further includes an illumination detection device 30, such as a CCD camera, disposed above the ring illumination apparatus 20, for example, at about 14 inches above the ring illumination apparatus 20. The illumination detection device detects light beams 32 reflected from each protruding reflective object 12 and creates a reflected image. One example of an illumination detection device 30 is a CCD camera having a resolution of about 640×480 pixels; although the present invention contemplates other types of cameras and devices capable of detecting an illuminated image.

The substantially ring-shaped light source 24 directs light beams 26 at angles of incidence with respect to the article 14 that cause non-detected light beams 34 to reflect from the flat or planar surfaces 18 on the article 14 outside of the field of view 16 or range of the illumination detection device 30. The preferred angles of incidence of the light beams 26 are in a range of less than or equal to about 100 and are provided by different embodiments of the substantially ring-shaped light source 24, as will be described in greater detail below. Accordingly, the detected light beams 32 reflecting from the reflective objects 12 create the reflected image and the non-detected light beams 34 reflecting from flat surfaces 18 are not included in the reflected image.

The ring illumination apparatus 20 can be mounted to a mounting support 28, for example, with a mounting bracket 29. The mounting support 28 and mounting bracket 29 support the ring illumination apparatus 20 in the desired position, allowing the article 14 to be disposed or positioned with the reflective objects 12 in the field of view 16. An article support surface 27 disposed beneath the ring illumination apparatus 20 supports the article to be inspected 14 so that the reflective surfaces 12 are in the field of view 16. In one example, the article support surface 27 is moved to index articles 14 successively into the field of view 16 for inspection during a manufacturing process, as is well known in the art. Alternatively, the ring illumination apparatus 20 and illumination detection device 30 are indexed or moved over each article 14 being inspected. When the articles 14 and/or ring illumination apparatus 20 and illumination detection device 30 are moved with respect to one another during inspection, the light source 24 preferably uses a strobed power supply that eliminates the effects of motion.

The inspection system 10 further includes an image processor 38 that processes the reflected image and determines inspection information including, but not limited to, the absence/presence, location, pitch, size, and shape of each protruding reflective surface 12, as will be described in greater detail below.

The inspection system 10 optionally includes a monitor 36 that allows the reflected image to be viewed by an operator. The monitor 36 facilitates the visual inspection and alignment of the reflective objects 12 by the operator. The present invention also contemplates other output or peripheral devices including, but not limited to, a printer or storage device. The image processor 38 can transmit the inspection information to the monitor 36 (if provided) for viewing by the operator or to other peripherals or devices, such as by digital I/O, RS-232 serial communication or Ethernet networking.

Figure 2:
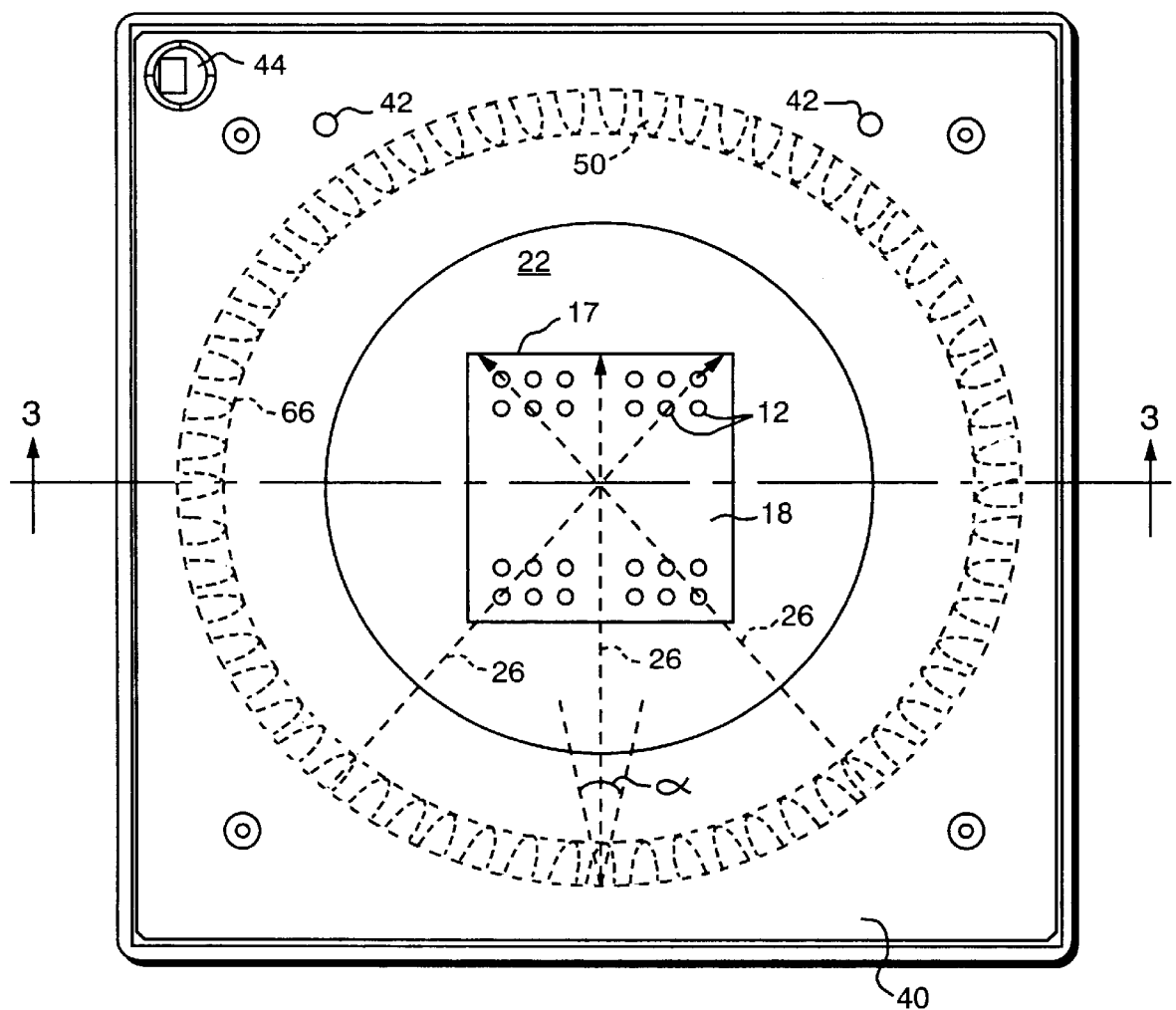
FIG. 2 is a top view of a ring illumination apparatus used to illuminate reflective elements in the inspection system and method according to one embodiment of the present invention.

The preferred embodiment of the ring illumination apparatus 20, FIG. 2, includes a mounting member 40 that defines the aperture 22 and is disposed above the article to be inspected 14. The mounting member 40 preferably includes one or more fastener receiving regions 42, for bolting or otherwise fastening to mounting bracket 29. The mounting member 40 can also include a power cord receiving region 44 that receives a power cord connected to a power source (not shown), for powering the light source 24. Although the exemplary embodiment uses a strobed power supply that eliminates the effects of motion on the illumination of articles 14, the present invention contemplates any type of power source.

The preferred embodiment of the substantially ring-shaped light source 24 includes a plurality of light emitting elements 50, such as light emitting diodes (LEDs), mounted to the mounting member 40 in a substantially ring shape. One example of each light emitting element 50 includes an LED that emits light beams having a far red spectral wavelength (e.g. about 660 nanometers) and a beam spread a of approximately 26° to 28°, such as a TLRA 155BP LED made by Toshiba. CCD cameras respond well to far red LED's which allow the effect of ambient light to be filtered out and substantially eliminated during the inspection process. In the exemplary embodiment, about sixty (60) of such LEDs 50 are mounted in a ring around the mounting member 40. The present invention contemplates any type and number of light emitting elements that provide the desired even illumination across the field of view.

Figure 3:
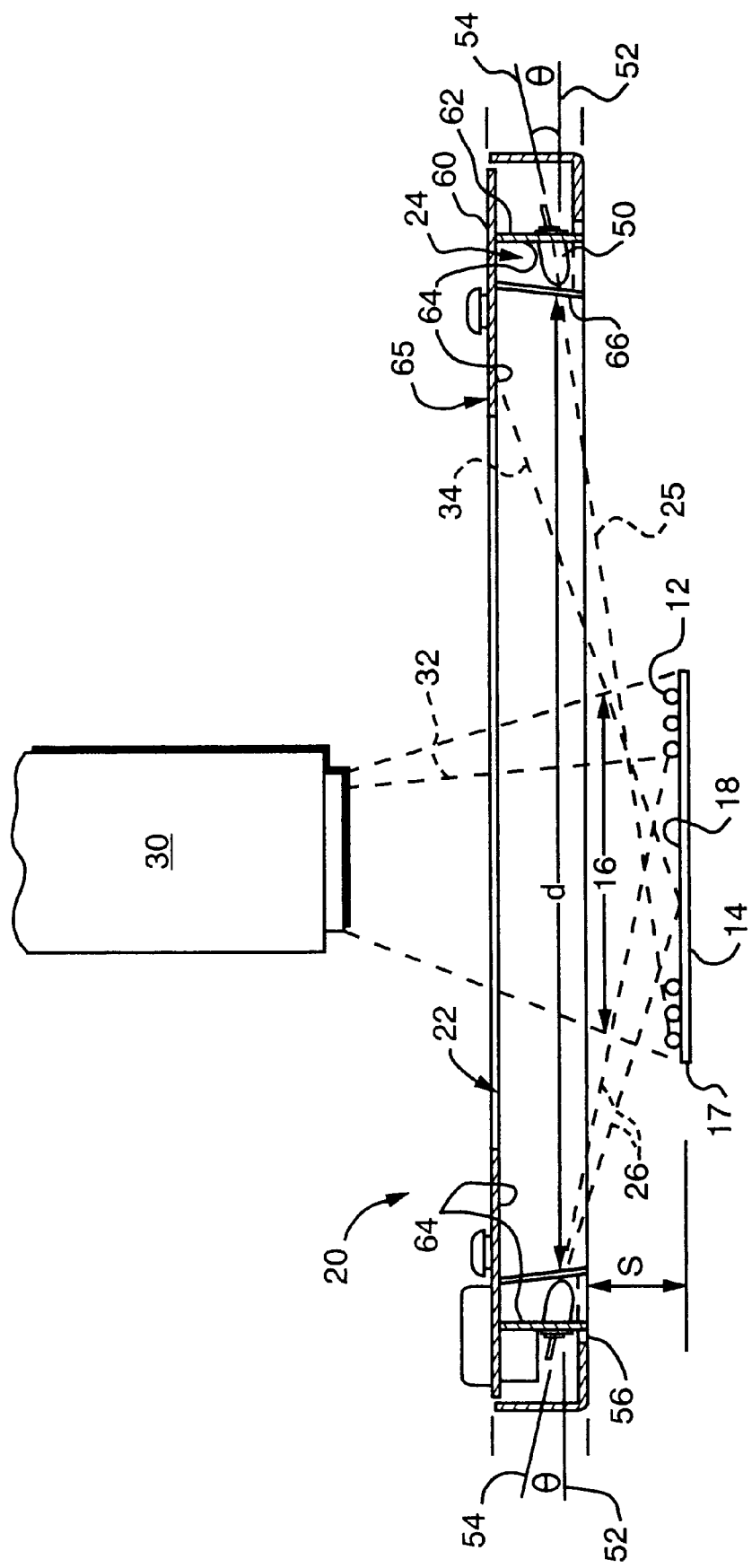
FIG. 3 is a side cross-sectional view of the ring illumination apparatus shown in FIG. 2 taken along line III—III.

According to one embodiment of the substantially ring-shaped light source 24, FIG. 3, the light beams 26 are directed at the article 14 in the desired range of angles of incidence by mounting the light emitting elements 50 so that a central axis or center line 54 of each light emitting element 50 is disposed at an angle θ with respect to a plane 52 parallel to the generally planar surface 18 of the article 14. A preferred angle θ of about 4° provides light beams 26 with a low angle of incidence (e.g. less than or equal to about 10°) onto the planar surface 18 of the article, such that the planar surface 18 (either non-reflective or reflective) will either not reflect the light beams 26 or will reflect the light beams 26 as non-detected light beams 34 that extend outside field of view 16 and are therefore not detected by the illumination detection device 30. This embodiment preferably includes a light reflecting surface 64, such as white paint or a reflective coating, proximate to each light emitting element 50 and may also include a light diffusing surface 66 generally in front of the light emitting elements 50, for scattering light and directing light more evenly across the article 14.

According to known light physics principles of reflectivity, when light hits a reflective surface, the angle of reflection is equal to the angle of incidence, measured from the axis perpendicular to the tangent of the reflective surface. If the angle θ of the light emitting element 50 is too large, the light emitting elements 50 will provide light beams 26 with a high angle of incidence and therefore a high angle of reflection, causing the light beams 26 to reflect off the planar surfaces 18 towards the illumination detection device 30.

Lowering the mounting angle θ of the light emitting elements 50 therefore lowers the angle of incidence of light beams 26 such that light beams 26 reflect from planar surfaces 18, such as reflective metalized pads and non-reflective flat surfaces, at a lower angle of reflection outside field of view 16 as non-detected light beams 34 that are not detected by detection device 30. The light beams 26 that hit the protruding reflective objects 12, on the other hand, will reflect through the aperture 22 to the illumination detection device 30 as detected light beams 32. The protruding reflective objects 12 are thereby illuminated for inspection while the planar surfaces 18 that are not being inspected are not illuminated.

In this embodiment, the angle θ of the light emitting elements 50 is also preferably greater than zero to allow sufficient spacing S between the ring illumination apparatus 20 and the article 14 being inspected while ensuring an even illumination across the entire field of view 16 on the article 14. The spacing S of the ring illumination apparatus 20 from the surface 18 allows articles 14 to be passed beneath the ring illumination apparatus 20 into and out of the field of view 16, e.g., when inspecting during a manufacturing process. The preferred spacing S is as small as possible without interfering with the article 14 passing beneath the ring illumination apparatus 20 during the inspection process, and typically in the range of about ¼ to ½ in. The light emitting elements 50 are also preferably positioned as close as physically possible to the bottom region 56 of the ring illumination apparatus 20.

The central light beam area 25 of light beam 26 directed along the center line 54 of each light emitting element 50 typically has the highest power or intensity. An angle θ of approximately zero (0) degrees will result in the central light beam area 25 being directed substantially parallel to the article 14. When the parallel central light beam area 25 is spaced from the article 14, the edges 17 of the field of view 16 on the article 14 will only receive lower power or intensity light beams, and protruding reflective objects 12 located proximate to the edges 17 of the field of view 16 may not be sufficiently illuminated.

By directing the central light beam area 25 towards the opposite sides or edges 17 of the field of view 16 on the article 14, a substantially even intensity of light beams is provided across the entire field of view 16 to provide a substantially even illumination of every protruding reflective object 12 located in the field of view 16. The angle θ of light emitting elements 50 is therefore defined so that an imaginary line extending from the center line 54 generally intersects or overlaps the opposite edges or sides 17 of the field of view 16, but without directing light beams 26 at an angle of incidence high enough to cause detection of light beams reflected from the planar surfaces 18.

The substantially ring-shaped light source 24 preferably forms a diameter d, e.g., measured from the front portion of the light emitting elements 50, of approximately 2.5 to 3 times a dimension or width of the field of view 16 on the article 14. This preferred diameter d allows the center light beam area 25 to be directed to the edges 17 with a low angle of incidence while maintaining sufficient spacing S between the ring illumination apparatus 20 and the article 14. In one example, a diameter of approximately 5.5 inches is used to evenly illuminate a field of view 16 on an article 14 of approximately 2 in. by 2 in. Accordingly, the diameter d of the ring-shaped light source 24 as well as the angle θ of the light emitting elements 50 allow the light beams 26 to provide even illumination across the field of view 16 on the article 14, while preventing illumination of unwanted planar surfaces 18 and allowing articles 14 to be passed beneath the ring illumination apparatus 20.

The preferred embodiment of the ring illumination apparatus 20 further includes an upper mounting portion 60 forming the aperture 22 and a side mounting portion 62 extending from the upper mounting portion 60. In the exemplary embodiment, the plurality of light emitting elements 50 are mounted to the side mounting portion 62 which is shaped as a ring and is welded or otherwise secured to the upper mounting portion 60. Either the light emitting elements 50 or the side mounting portion 62 can be angled to provide the angle θ.

The light diffusing surface 66 can be formed as a light diffusing member or ring mounted to the upper mounting portion 60. The present invention contemplates other types of surfaces that diffuse or scatter the light from the light source, such as a light diffusing surface directly disposed on each individual light emitting element 50.

The light reflecting surface 64, such as white paint or other light reflecting colors, can be provided on the side mounting portion 62 and upper mounting portion 60. In one embodiment, the diameter of the aperture 22 is approximately 70 to 80 percent the diameter d of the substantially ring-shaped light source 24 such that a portion 65 of the upper mounting portion 60 extends beyond the light emitting elements 50 and has a light reflecting surface 64.

Figure 4:
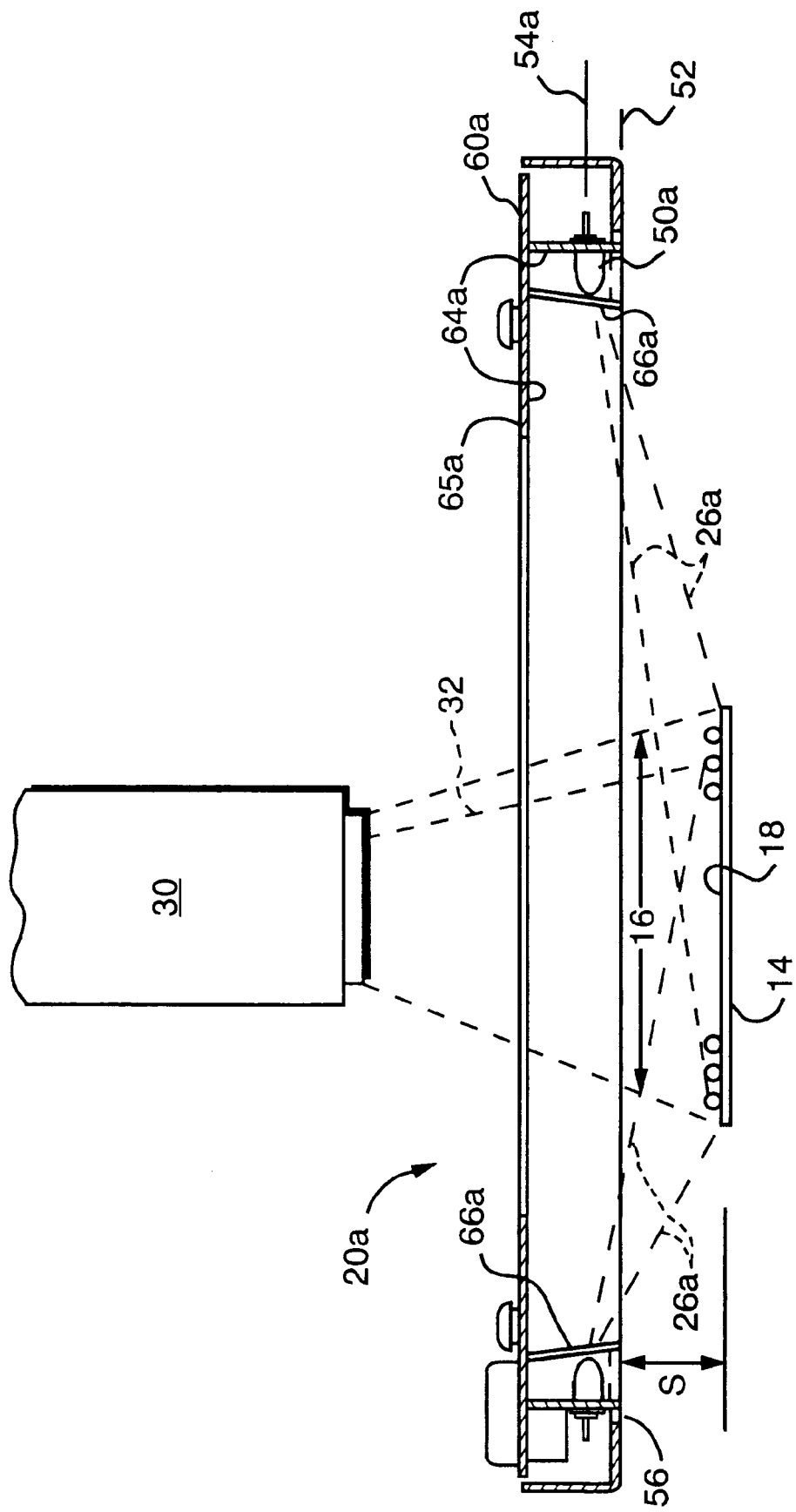
FIG. 4 is a side cross-sectional view of the ring illumination apparatus according to another embodiment of the present invention.

In accordance with another embodiment of the ring illumination apparatus 20a, FIG. 4, the light beams 26 are directed at the article 14 in the desired range of angles of incidence with a high transmissivity, high diffusion diffuser 66a that disperses and angularly scatters light beams as they are emitted from the light emitting elements 50a. The angularly scattered light beams 26a provide the substantially even intensity of light across the field of view 16 on the article 14 while preventing illumination of the flat reflective surfaces and allowing the spacing S from the ring illumination apparatus 20a. In this embodiment, the angle θ of the of the light emitting elements 50 can be eliminated and is preferably in a range of 0° to 80°.

When the high transmissivity, high diffusion diffuser 66a is used, a light reflecting surface 64 is not provided on the portion 65a of the upper mounting portion 60a that extends beyond the diffuser 66. This portion of the upper mounting portion 65a can have a black or other non-reflective surface or can be eliminated entirely.

The high transmissivity, high diffusion diffuser 66a has a diffuse transmission of about 85% or more and preferably in the range of about 88% to 90%. One type of high transmissivity, high diffusion diffuser 66a is an acrylic Diffusing Film Alternative (DFA) manufactured by 3M™. The present invention also contemplates other suitable high transmissivity, high diffusion films that provide the desired diffuse transmission and the desired angular scattering of the light beams.

A larger ring light apparatus can be used for larger fields of view. For tighter applications, a smaller ring light can be used with conical mirrors that fold the optical path to preserve the internal light path and direct the light beams at the article in the desired angle of incidence range.

The method of using the inspection system 10 to inspect one or more reflective elements, such as reflective objects 12, disposed on the article 14 includes positioning the article 14 in the field of view 16. Either a series of articles 14 are sequentially passed or indexed through the field of view 16 beneath the ring illumination apparatus 20 or the ring illumination apparatus 20 is indexed over each article 14. A ring of light beams 26 is directed in a desired range of angles of incidence from the ring illumination apparatus 20 toward the reflective element(s) 12 in the field of view 16 containing, to provide a substantially even intensity of light beams across the field of view 16 without illuminating planar surfaces 18 on the article 14.

Figure 5:
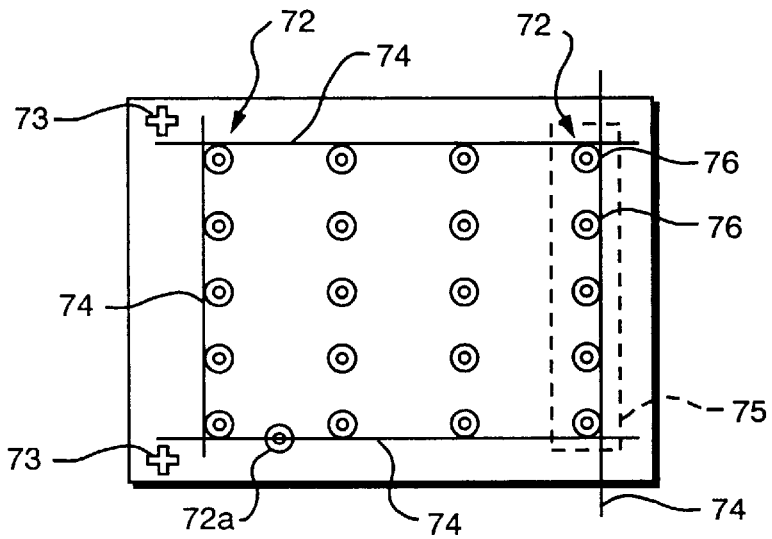
FIG. 5 is a schematic view of a reflected image detected by the inspection system according to one embodiment the present invention.

The system and method of the present invention detects light beams reflected from the illuminated reflective elements, such as protruding reflective objects 12, to form a reflected image 70, FIG. 5, of the illuminated reflective elements. The reflected image includes reflected image elements 72 representing the illuminated reflective elements, such as reflective objects 12. The reflected image 70 is acquired by converting the analog output signal of the illumination detection device (camera) 30 into a plurality of digital signals, each representing a small picture element or pixel of the image. The digital signals forming the reflected image 70 can then be converted to analog signals for display on the monitor 36 and/or processed by the image processor 38 (see FIG. 1).

Figure 6:
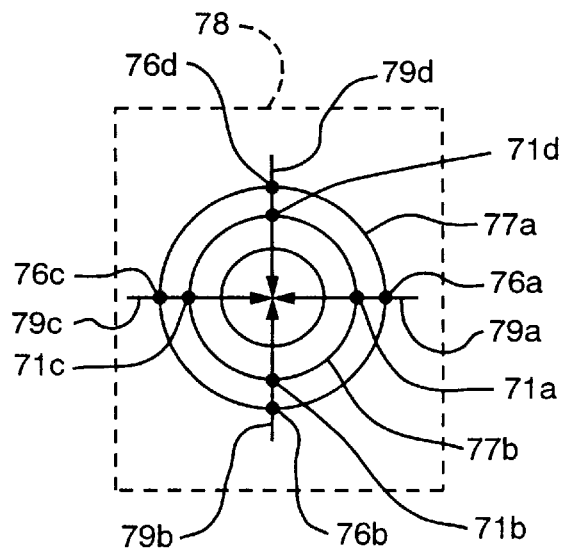
FIG. 6 is a schematic view of a single reflected image element to be processed according to one embodiment of the present invention.

The reflected image 70 is processed to determine inspection information including, but not limited to, absence/presence, location, size, and shape of the reflective elements. In the exemplary system and method, which is not intended to limit the present invention, the inspection system 10 is used to inspect an array of solder balls disposed on solder pads on an electronic component, such as a semiconductor chip. In the reflected image 70, each solder ball appears as a reflected image element 72, FIG. 6, having a "doughnut" or ring shape. The inspection information pertaining to the array of solder balls includes, but is not limited to, absence/presence of each solder ball in the array, location of each solder ball, the pitch between solder balls, malformed solder balls, the diameter of each solder ball, and the circularity of each solder ball.

Figure 7:
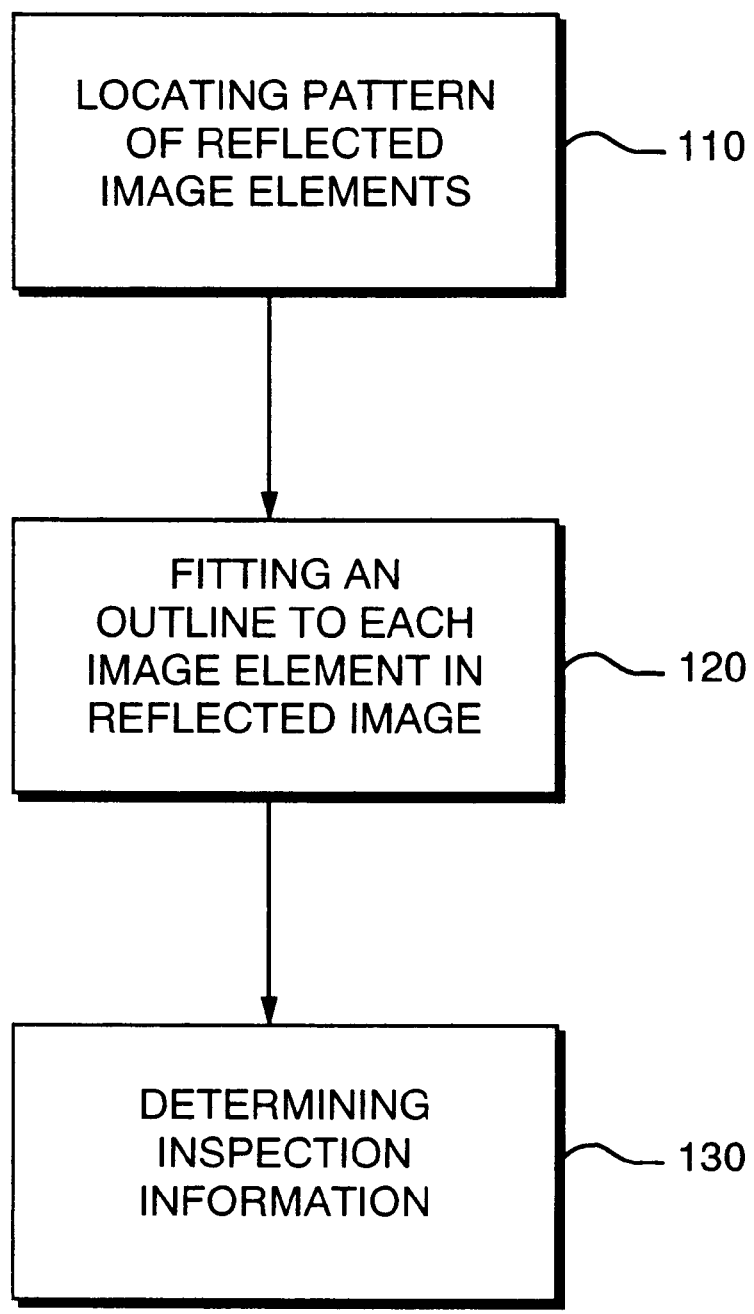
FIG. 7 is a flow chart of a method for processing a reflected image according to the present invention.

The present invention also features a method 100, FIG. 7, of processing a reflected image 70 including a pattern of reflected image elements 72. The method of processing the reflected image includes locating the pattern of reflected image elements 72 in the reflected image 70, step 110; fitting an outline to each reflected image element 72 in the pattern of reflected image elements, step 120; and determining inspection information pertaining to the reflective elements represented by the reflected image 70, step 130.

One way of locating the pattern of reflected image elements 72, step 110, is by identifying a group of reflected image elements 72, for example, by creating a window 75 (FIG. 5) around an outside row or group of reflected image elements 72. A point on each reflected image element 72 in the group, such as an outside edge 76, is then located. One or more lines 74 are fit to the outside edges 76 or other point on the reflected image elements 72 (see FIG. 5) to locate the pattern and determine the "expected" location of each reflected image element 72 in the pattern. Although the exemplary embodiment shows a rectangular grid of image elements 72, the present invention also contemplates locating a circular or other pattern of reflected image elements. In a circular pattern, the outside edges of the image elements formed in a circle are located and a circle fit algorithm is used to fit a circle to the outside edges and to locate the pattern.

Another way of locating the reflected image is by locating reference marks or fiducials 73 disposed in predetermined locations with respect to the reflected image elements 72 in the reflected image 70. A further way of locating the reflected image is by correlating a template or model of a known pattern with the reflected image.

Once the pattern of the reflected image 70 is located, the outline is fit to each reflected image element, step 120, for example, by creating a window 78 (FIG. 6) around each reflected image element 72 at each expected location and locating multiple points 76a–76d on the edge 76 of the reflected image element 72 or locating multiple midpoints 71a–71d within the reflected image element 72. For a reflected image element 72 having a circular or ring shape, at least three of the edge points 76a–76d or midpoints 71a–71d are needed to fit the respective circular outline 77a, 77b. Four edge points 76a–76d or midpoints 71a–71d are needed to determine the circularity of the respective outline 77a, 77b. The edge points 76a–76d or midpoints 71a–71d and respective outlines 77a, 77b fit to the image element(s) 72 correspond to a known percentage of the true the diameter, circularity, or other dimension of the solder ball or other reflective element being measured, as described in greater detail below. In the preferred embodiment, eight (8) or more points are located, and the locations of the points are fed to a circle fit algorithm which accurately determines the size and circularity of the reflective elements.

Figure 8:
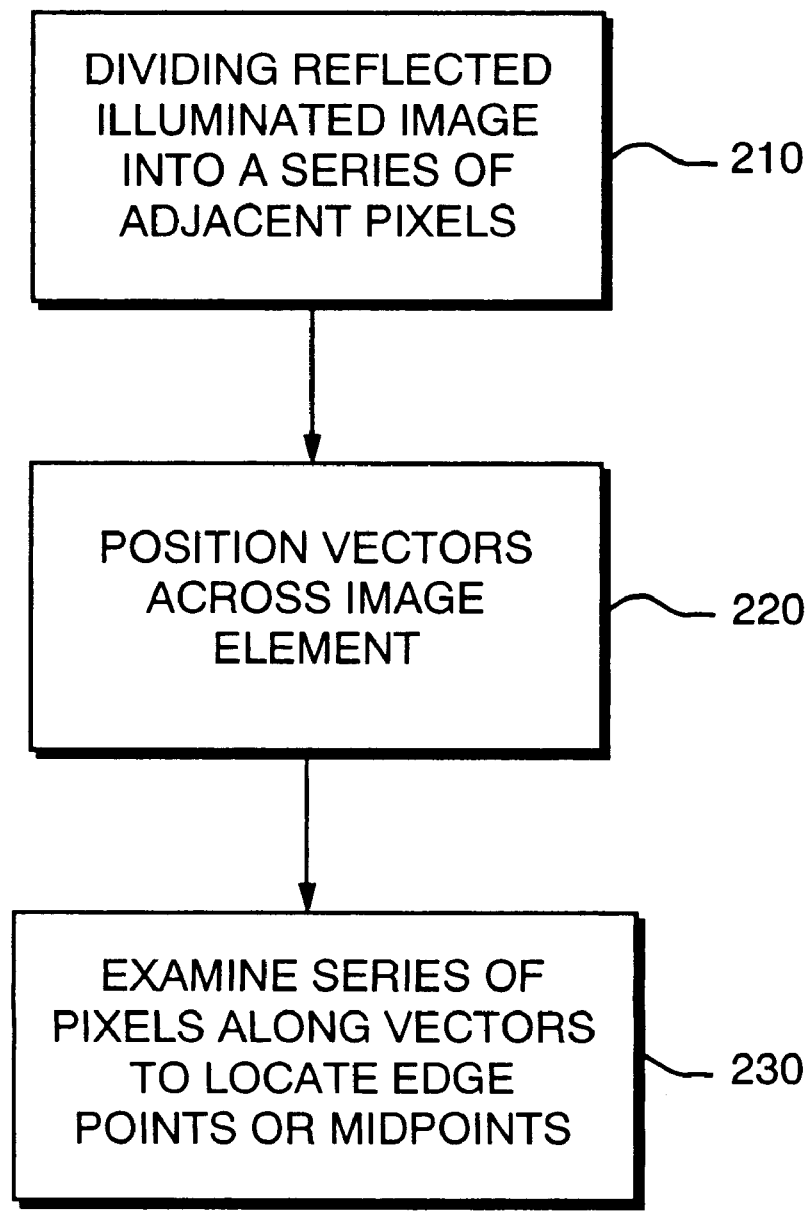
FIG. 8 is a flow chart of a method for locating one or more points on a reflected image element in a processed reflected image according to the present invention.

The method 200, FIG. 8, of locating the points 76a–76d on the outside edge 76 or the midpoints 71a–71d of each reflected image element 72 includes dividing the reflected image 70 into a plurality of pixels having a gray scale value corresponding to an intensity level of reflected light in the reflected image 70, step 210. In one example, each pixel is represented by eight (8) bits with a gray scale value of zero (0) being the darkest pixel and a gray scale value of 255 being the brightest pixel. Vectors 79a–79d (FIG. 6) are positioned to intersect the expected location of the image element 72, step 220. A series of pixels along each vector 79a–79d is examined to find edge points 76a–76d or midpoints 71a–71d, step 230, along the vectors 79a–79b. Although shown as radial vectors, the vectors can be positioned in various configurations, such as a cross-hatched configuration, provided that the vectors intersect the image element 72. The edge points 76a–76d or midpoints 71a–71d are then used to locate the image by fitting the line 74 or to determine a diameter, circularity or other dimension of the solder ball by fitting the outline 77a, 77b, as describe above.

To locate the edge points 76a–76d along the path of each vector 79a–79d, an intensity gradient at each pixel is determined by differentiating between the gray scale values of pixels on either side of each pixel. The point of maximum gradient (i.e. the steepest or greatest change from darkest to brightest pixels) is located and is assigned to correspond to the edge 76 of the reflected image element 72. The preferred method includes taking a group of points having the highest intensity gradients for each reflected image element 72 and fitting an ellipse to the highest intensity gradients. The peak of the ellipse corresponds to the point of highest intensity gradient with sub-pixel accuracy, thereby allowing a more accurate calculation of the dimensions and shape of the solder ball or other reflective surface represented by each reflected image element 72. The edge points 76a–76d and circular outline 77a fit to the edge points 76a–76d correspond to a known percentage of the true dimensions of the solder ball being measured, e.g. about 70%.

To locate the midpoints 71a–71d along the vectors 79a–79d, a gray scale value at each pixel is determined and the midpoint 71 in the ring shaped image element 72 corresponds to the pixel having the highest gray scale value. The preferred method includes taking a group of pixels having the highest gray scale value, e.g. the brightest pixel and one or more adjacent pixels, and fitting an ellipse to these pixels. The peak of the ellipse corresponds to the midpoint 71 having the highest intensity with sub-pixel accuracy.

Figure 6A:
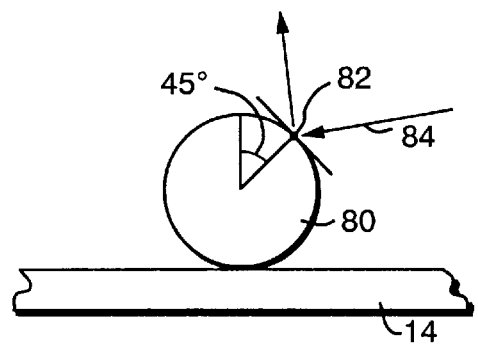
FIG. 6A is a side schematic view of a solder ball with light beams reflecting from the point of maximum reflection.

The brightest midpoints 71a–71d and the circular outline 77b fit to midpoints 71a–71d correspond to a known dimension of the solder ball being measured. Each solder ball 80, FIG. 6A, has point 82 of maximum reflection located on the spherical surface of the solder ball 82 at about 45° from the top that reflects light beams 84 of the highest intensity. The location of the point 82 of maximum reflection is equal to sin(45) (or 0.7071) times the diameter of the solder ball 80. The brightest midpoints 71a–71d and the circular outline 77b therefore correspond to the point(s) 82 of maximum reflection and the known percentage of the true diameter of the solder ball 80. Using the brightest midpoint 71a–71d of the image element 72 provides a truer measurement than using the intensity gradient method to locate the edge points 76a–76d of the image element 72 if the edges 76 of the image elements 72 are not focused.

Figure 9:
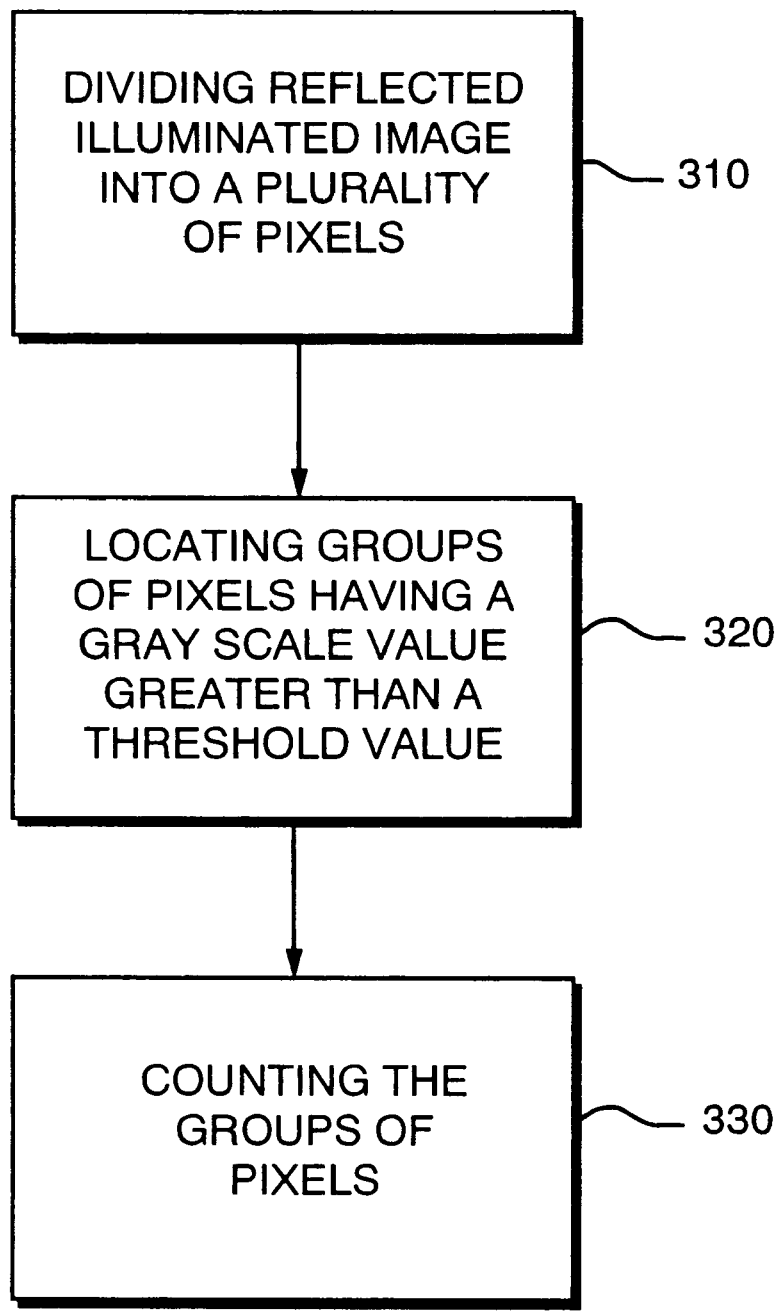
FIG. 9 is a flow chart of a method for determining a number of reflected image elements in a reflected image according to the present invention.

Since the method above processes the reflected image elements 72 according to their expected locations as determined by fitting the lines 74 along the edges 76 (FIG. 5), an extra or additional reflected image element 72a corresponding to an added solder ball or other reflective surface may not be detected. The present image processing method further includes a method 300, FIG. 9, of determining the number of reflected image elements 72. Determining the number of reflected image elements 72 in the entire reflected image 70, not just at the expected locations, allows the absence/presence of solder balls or other reflective surfaces to be easily determined.

The number of reflected image elements 72 is determined by dividing the reflected image 70 into a plurality of pixels having a gray scale value corresponding to the intensity of light in the reflected image 70, step 310. Groups of pixels having a gray scale value above a threshold value are then located, step 320, and the number of groups of pixels (corresponding to the number of reflected image elements 72) are counted, step 330. Determining the number of reflected image elements 72 allows a determination of missing, misplaced or extra reflective elements, such as solder balls or other reflective objects.

The image processing method of the present invention also includes a calibration process that can be performed to allow the inspection information measurements to be expressed in conventional units and to correct for magnification, perspective errors, and other effects. The calibration procedure involves measuring a target of known dimensions, for example, an array of dots having known sizes and known locations on the target. The relationship between the coordinates of the target image as determined by the image processor and the known location of the dots on the target are calculated to determine the correlation between pixels and conventional units. The present method also contemplates height correction of the part being inspected relative to the calibration target to account for errors caused by optical magnification.

The present method for processing the reflected image 70 used together with the ring illumination apparatus 20 described above provides a more accurate determination of the diameter and circularity of solder balls on an electronic component or other article. Directing the light beams in the desired range of angles of incidence, e.g. by angling the light source 24 at an angle θ, by using a high diffusion diffuser, or by using conical mirrors, illuminates a portion of the top surface of each solder ball so that the point of maximum gradient or highest gray scale value corresponds to a known percentage of the true diameter of the solder ball. Directing the light beams in the desired range of angles of incidence, also prevents illumination of solder pads or other generally planar surface areas from interfering with the determination of the maximum gradient.

When the ring illumination apparatus of the present invention is used together with the present method of processing the reflected image, the measurements made during the inspection have a high degree of accuracy and repeatability. The present invention, however, contemplates using the ring illumination apparatus with other methods for processing the reflected image as well as using this method of processing the reflected image with another type of illumination apparatus.

Figure 10:
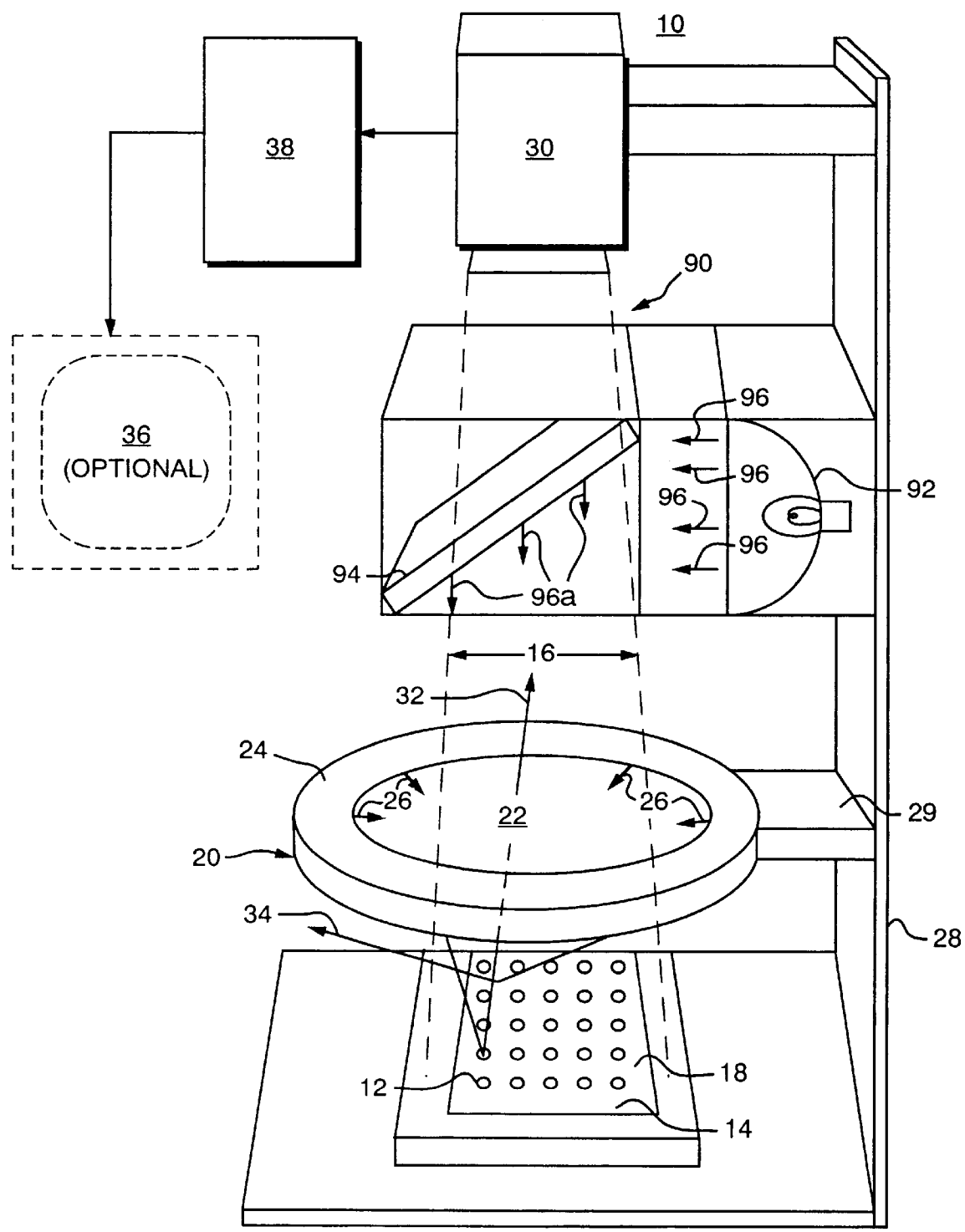
FIG. 10 is a schematic view of an inspection system for inspecting one or more surfaces or objects according to an additional embodiment of the present invention.

One such alternative embodiment is shown in FIG. 10. In this embodiment, a second illumination apparatus 90 is added to the ring illumination apparatus and inspection system described in detail above. (Common elements found in the embodiments of FIGS. 1 and 10 are designated using common reference numbers.) The apparatus of FIG. 10 uses the principle of image subtraction to eliminate or mask the unwanted features of the image. For example when a ball and bumped grid array (BGA) is inspected both the solder balls, which are desired to be inspected, and solder vias intermediate the balls may appear similarly when the BGA is illuminated by a single illumination apparatus.

The principle of image subtraction requires the illumination of the article to be inspected by at least two different illumination apparatuses and the capturing of at least two different images of the article as it is illuminated using the different illumination apparatuses. The different illumination apparatuses are selected so that they illuminate the unwanted features similarly, while at the same time illuminate the desired features differently. Thus, when one image is subtracted from the other image, the unwanted features, which appear substantially the same in both images, subtract out to 0. However, since the desired features appear different in the two captured images, they do not subtract out. In fact, they will either remain the same or be enhanced by the image subtraction process. Thus, the image resulting from the image subtraction process will contain only the desired features, which can then be analyzed further using additional image processing equipment and methods.

In the embodiment of FIG. 10, a second illumination apparatus is mounted to mounting support 28. The second illumination apparatus is an on-axis illumination apparatus 90, which provides on-axis illumination of the article to be inspected 14, substantially co-linearly with the illumination detection device 30. The on-axis illumination apparatus 90 includes light source 92 and beam splitter 94. The beam splitter 94 is positioned within the field of view 16 and, in the preferred embodiment is located above the ring illumination apparatus 20.

The beam splitter 94 re-directs the light beams 96 generated by light source 92 towards the article to be inspected. Preferably, the re-directed light beams 96a are substantially co-linear with the axis of the illumination detection device 30 in order to provide the desired effects of the use of multiple illumination apparatuses, which will be discussed in more detail below.

Figure 11:
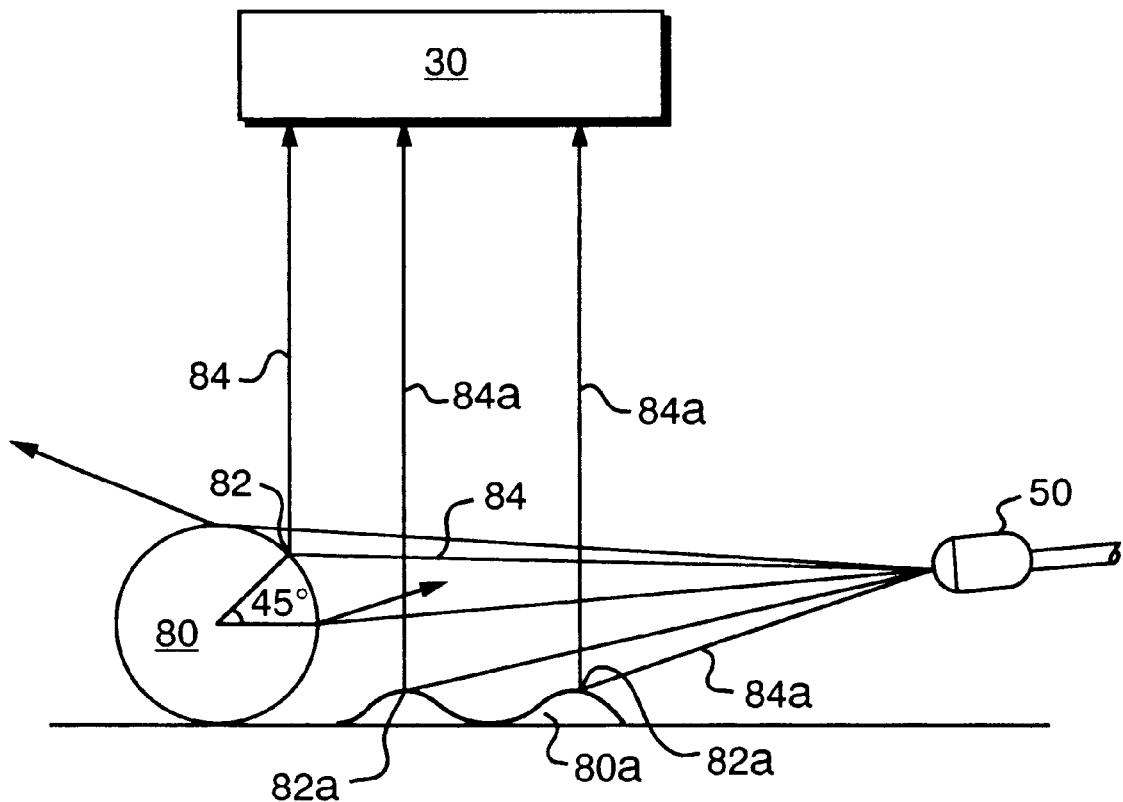
FIG. 11 is a side schematic view of a solder ball and a solder via illuminated with light beams from a low angle ring light source showing light beams reflecting from the points of maximum reflection.

FIG. 11 shows the orientation of a solder ball 80 and a solder via 80a on a BGA being inspected by the inspection apparatus 10. As explained with respect to FIG. 6A earlier, each solder ball 80 has point 82 of maximum reflection of light beam 84, which is located on the spherical surface of the solder ball 82 at about 45° from the top of the ball. This location of maximum reflection 82 directs reflected light beams 84a of the highest intensity. Likewise, each solder via 80a has points 82a of maximum reflection located substantially adjacent to each peak of the solder via 80a, where the surface of the solder via is oriented substantially 45° with respect the axis of the illumination detection device 30. (In reality, the solder ball 80 and solder via 80a are three-dimensional objects, the former being a sphere and the later being a disc having a circular shaped ring of maximum thickness.)

Figure 13:
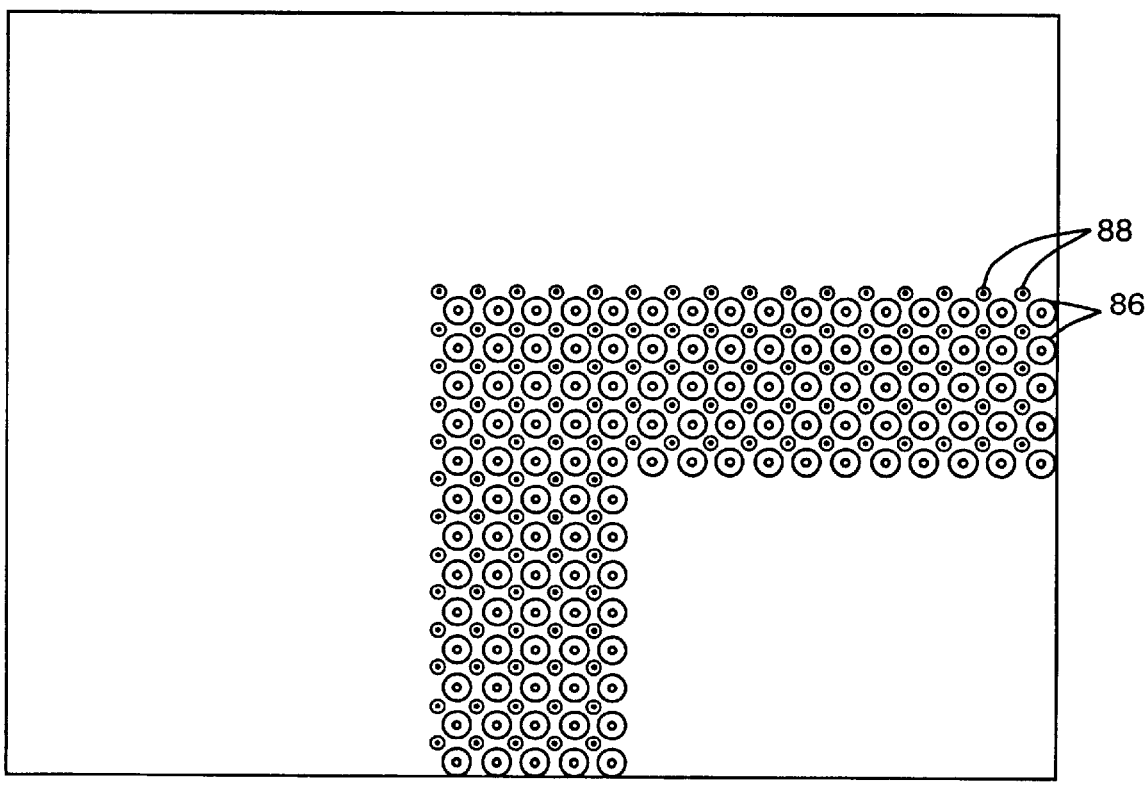
FIG. 13 is an image of a ball and bumped grid array (BGA) illuminated with a low angle ring light source showing both desired and unwanted features.
Figure 16A:
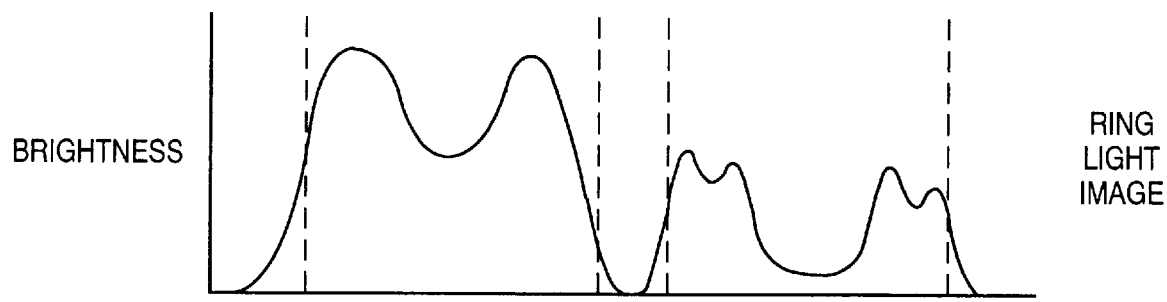
FIG. 16A is a graphical depiction of illumination brightness with respect to position along the solder ball and solder via of FIG. 11, when the BGA is illuminated with a low angle ring light source.

When the BGA is inspected with the ring illumination apparatus 20, as shown in FIG. 11, the resulting image captured by the illumination detection device 30, will appear as a grid of illuminated rings (FIG. 13). These illuminated rings correspond to the 45 degree surfaces of the solder balls and the solder vias, which reflect light from the ring light source 20 into the illumination detection device. The solder balls 80 appear as large bright rings 86 and the solder vias appear as smaller bright rings 88. A two-dimensional graph of image brightness with respect to position on each solder ball and solder via illuminated using the ring illumination source according to FIG. 11 is shown in FIG. 16A. However, the bright rings that represent the solder vias are similar in brightness to those that represent the solder balls. Accordingly, they may interfere with the image analysis. Thus, their elimination from the image to be analyzed is desirable.

The article to be inspected 14 is next illuminated by the second, different illumination apparatus and a second image of the article is captured by the illumination detection device 30. For example, the article may be illuminated by an on-axis illumination apparatus 90 (FIG. 10). An on-axis illumination apparatus is selected since it will illuminate the article to be inspected 14 in such a manner that the solder vias 80a will appear substantially the same to the illumination detection device 30 as they appear when illuminated using the ring illumination apparatus of FIG. 11.

Figure 12:
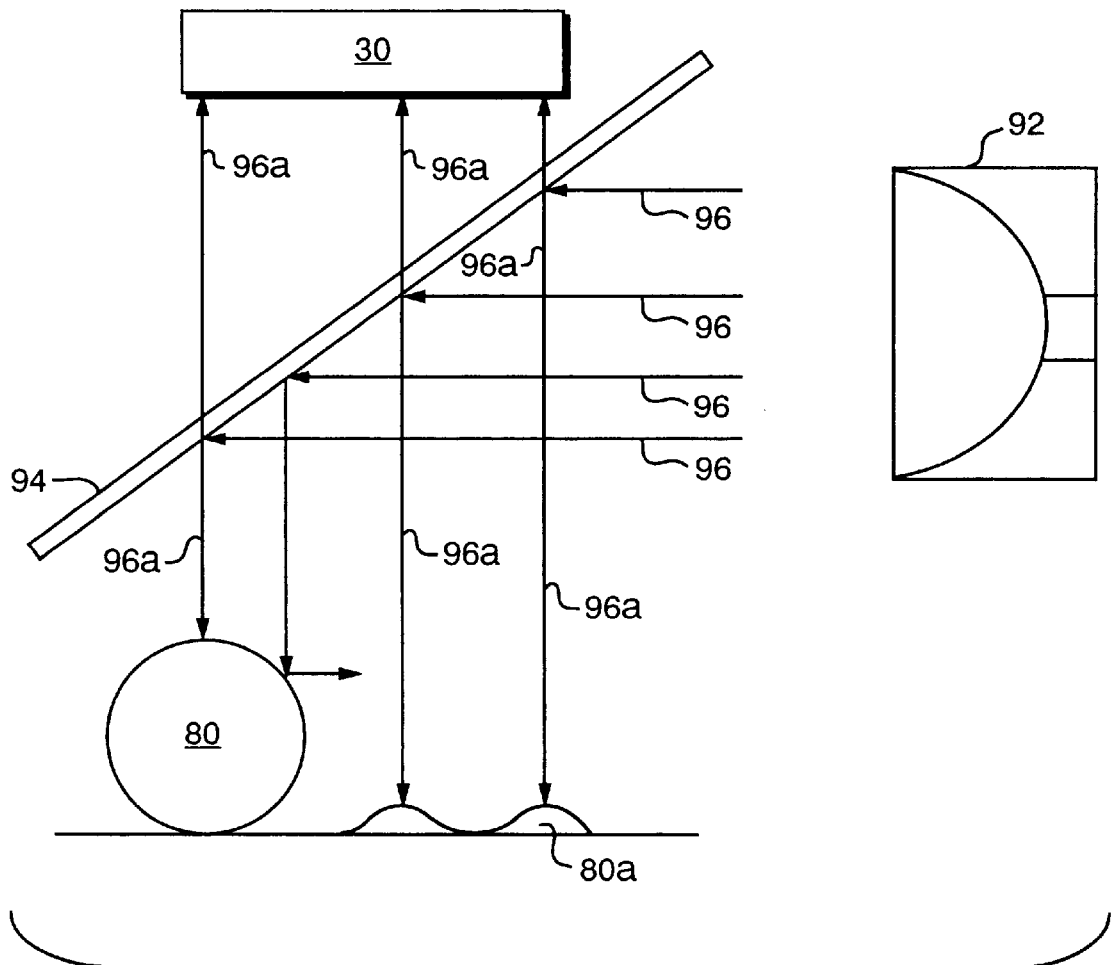
FIG. 12 is a side schematic view of a solder ball and a solder via illuminated with light beams from an on-axis light source, colinear with the illumination detection device showing light beams reflecting from the points of maximum reflection.

The geometry of the incident and reflected light rays from on-axis illumination apparatus are shown in FIG. 12. Light rays 96 are emitted from light source 92 and are directed to beam splitter 94, which reflects the light rays toward the solder balls 80 and solder vias 80*a* as incident light rays 96*a*, which are substantially colinear with the axis of the illumination detection device 30. As can be seen, only those incident light rays 96*a* that reflect off of horizontal surfaces will be reflected back up to the illumination detection device 30, where they will be captured as a second image of the article being inspected 14.

Figure 14:
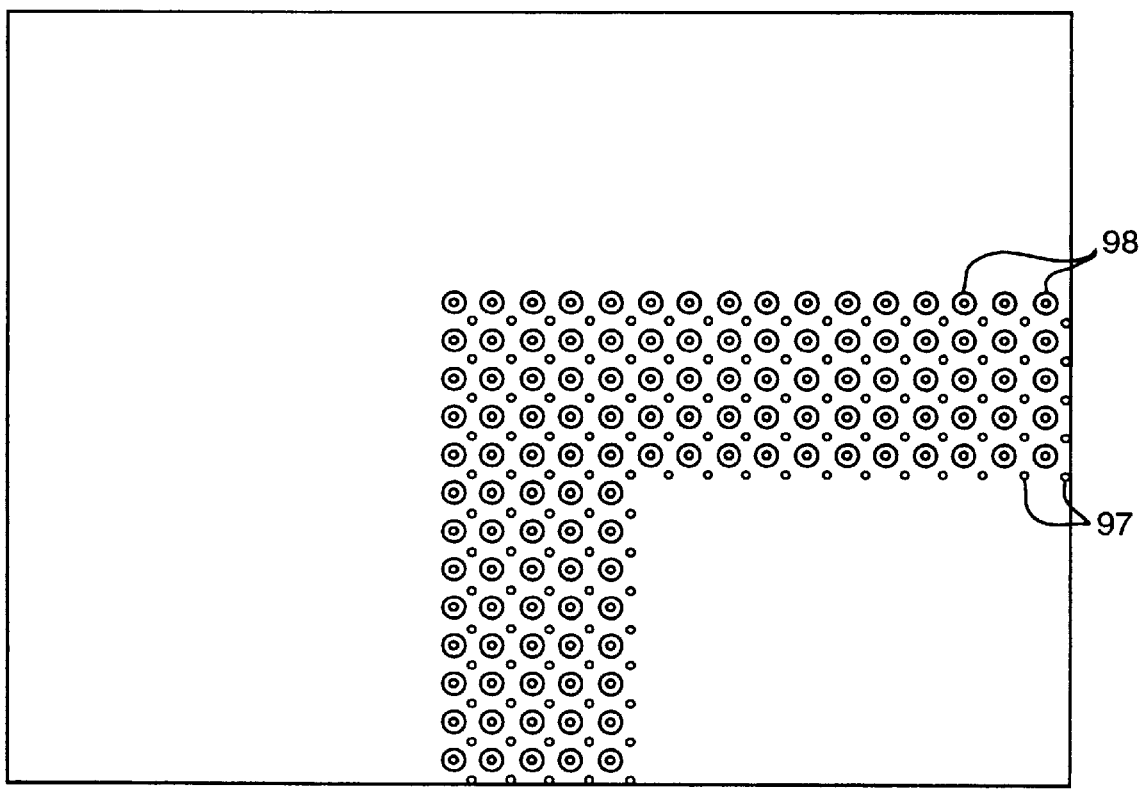
FIG. 14 is an image of the same ball and bumped grid array (BGA) shown in FIG. 13, which is illuminated with an on-axis light source, colinear with the illumination detection device, which also shows both desired and unwanted features.

The second image of the article is shown in FIG. 14 and includes a plurality of bright dots 97 and bright rings 98. The bright dots are the reflections received from the top of the solder balls 80. The solder vias 80*a* appear as the bright rings 98 because the incident light rays 96*a* reflecting off the flat top of the crater-like via is captured by the illumination detection device 30.

Figure 16B:
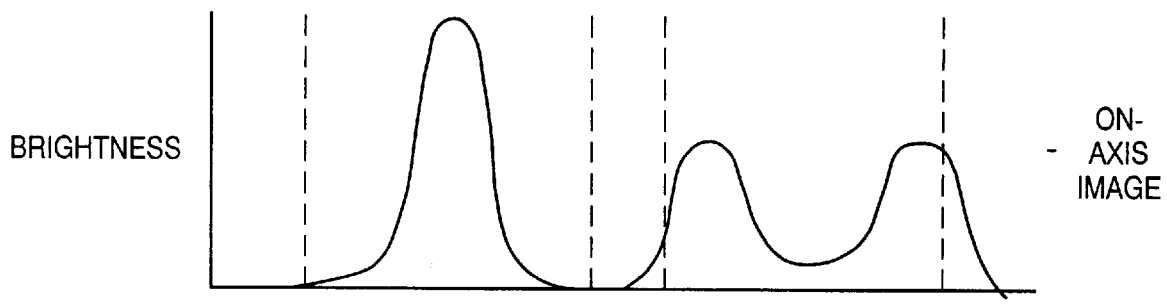
FIG. 16B is a graphical depiction of illumination brightness with respect to position along the solder ball and solder via of FIG. 12, when the BGA is illuminated with an on-axis light source, colinear with the illumination detection device.

A two-dimensional graph of image brightness with respect to position on each solder ball and solder via illuminated using the on-axis illumination source according to FIG. 12 is shown in FIG. 16B. When the graph of image brightness of the solder vias of FIGS. 16A and 16B are compared, it is evident that the images of the solder vias are substantially the same, although not identical.

Figure 16C:
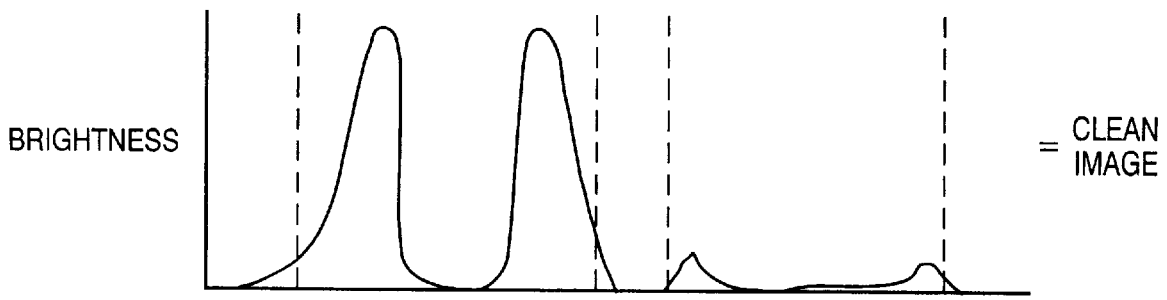
FIG. 16C is a graphical depiction of illumination brightness with respect to position along the solder ball and solder via of the resulting image calculated by subtracting the image of FIG. 16B from the image of FIG. 16A.

According to the principle of image subtraction, the second captured image, which is the image captured when the article is illuminated using the on-axis illumination apparatus is then subtracted from the first captured image, which is the image captured when the article is illuminated using the ring illumination apparatus. As can be seen in FIG. 16C, the result of image subtraction is that the images of the solder vias substantially cancel each other out, while the image of the solder balls do not. Thus, the resulting image would only include the desired features, which, in this case are the solder balls.

Figure 15:
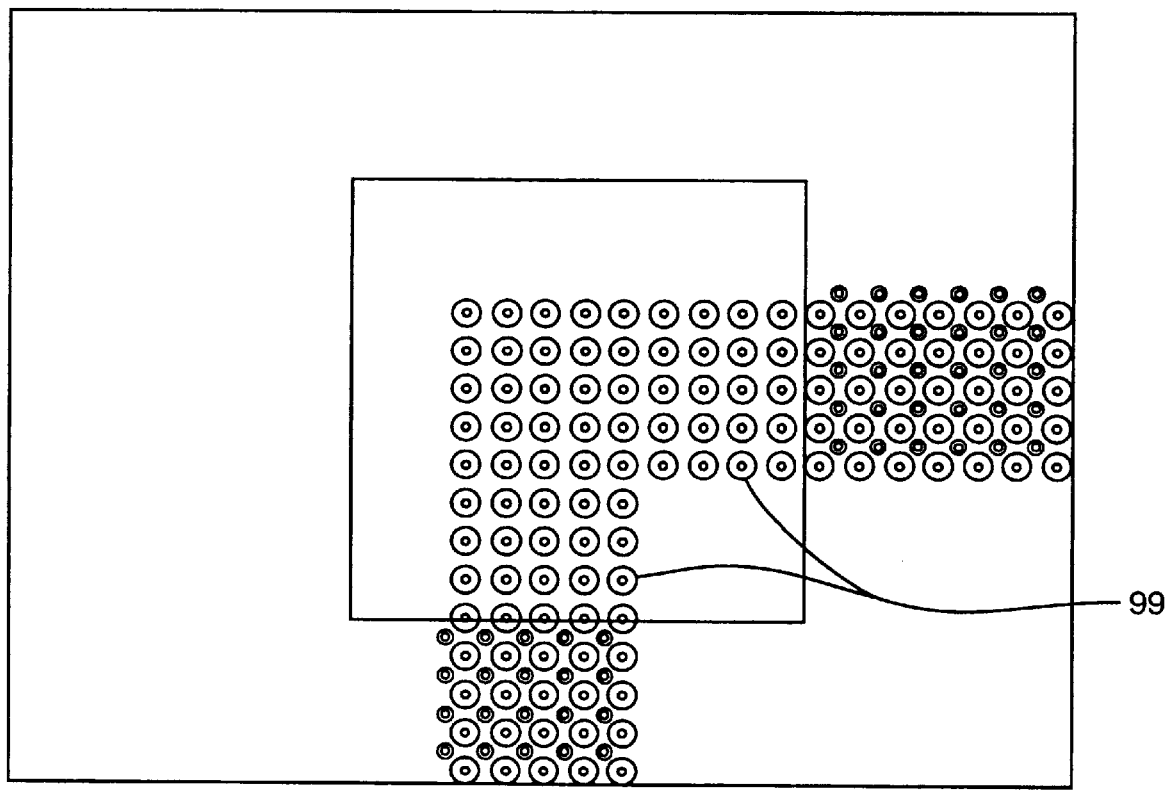
FIG. 15 is the resulting image calculated by the image processor of the present invention, wherein the image of FIG. 14 is subtracted from the image of FIG. 13, thus eliminating the unwanted features and showing the desired features.

The image resulting from the above-specified image subtraction operation is shown in FIG. 15. As can be seen from this image, the unwanted features, namely the solder vias, are eliminated within the search box. However, the solder balls, which are the desired features of the article being inspected appear as bright rings 99.

Figure 17:
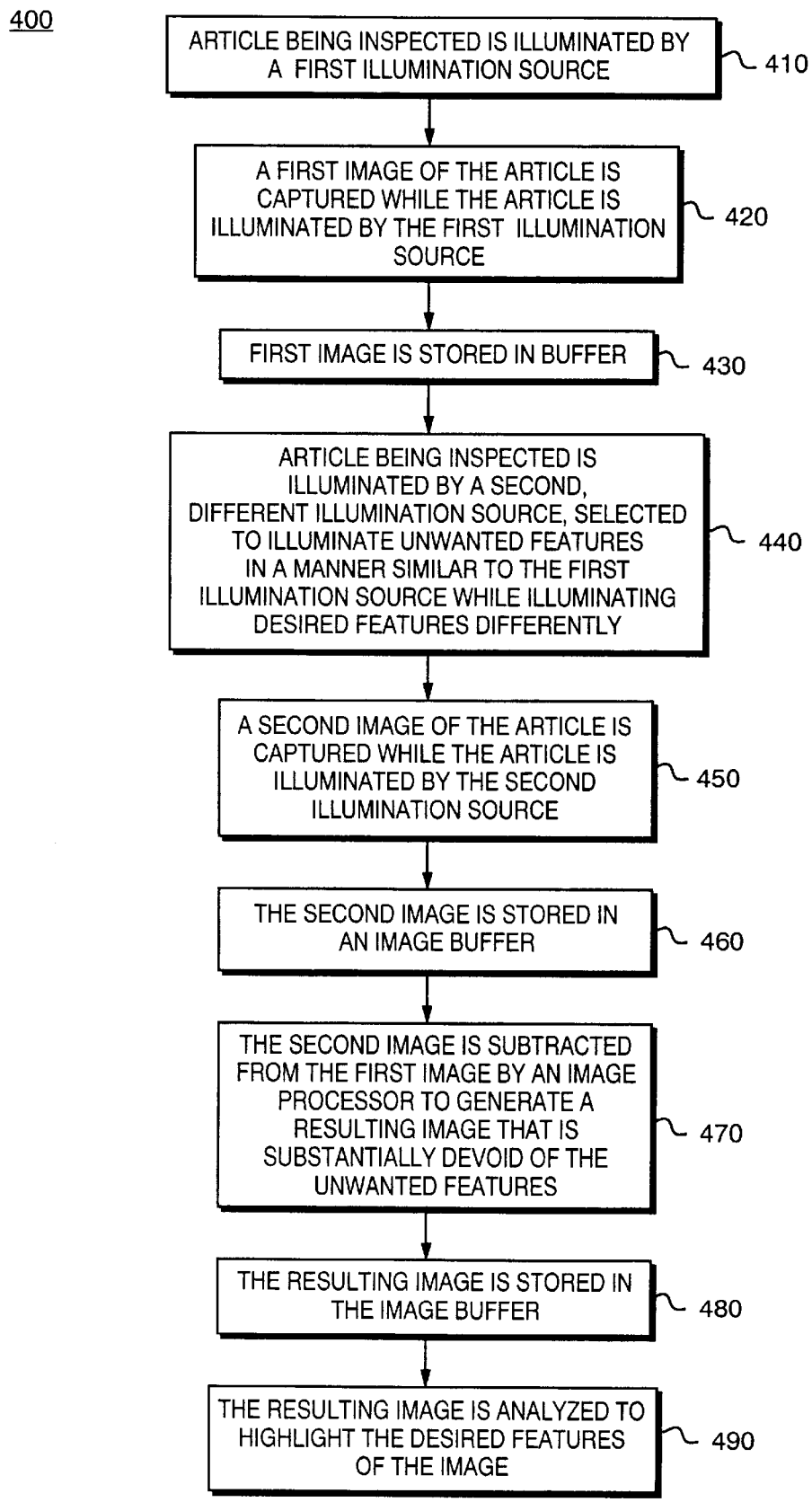
FIG. 17 is a flow chart of a method of inspecting a BGA to highlight features of interest for image analysis while masking unwanted features according to the teachings of the present invention.

A method of image subtraction 400 is shown in FIG. 17. The method begins by illuminating an article to be inspected with a first illumination apparatus, step 410. Once the article is illuminated, a first image of the article is captured using an illumination detection device, such as a CCD camera, step 420. The first image is then stored in an image buffer, step 430.

The article to be inspected is then illuminated by a second illumination apparatus, which is selected such that the desired features of the article will be illuminated differently by the second illumination apparatus than they were with the first illumination apparatus and the unwanted features will be illuminated substantially the same as they were illuminated by the first illumination apparatus, step 440. Then, a second image of the article is captured by the image capture device, step 450, an is stored in the image buffer, step 460.

The images are then processed by an image processor, which subtracts one image from the other to generate a resulting image, step 470. In one case, the first image may be subtracted from the second image. In another case, the second image may be subtracted from the first. However, in both cases, since the unwanted features appear substantially the same in both the first and second captured images, the subtraction process will substantially eliminate them from the resulting image. Thus, the resulting image will be substantially devoid of the unwanted features.

The resulting image will then be stored in the image buffer, step 480. The resulting image may then be analyzed using additional image analysis techniques.

Of course, there may be multiple classes of unwanted features on an article being inspected. In this case, it may be necessary to illuminate the article with a third or more illumination apparatuses and third and additional images will need to be captured and processed by the image processor to eliminate all unwanted features. Therefore, multiple image subtraction processes are contemplated by the disclosed invention.

Accordingly, the present invention provides, an inspection system and method that accurately inspects and measures one or more surfaces or objects, such as solder balls, protrusions, intrusions, deviations, concavities, and other reflective elements on an article. The image subtraction system and method illuminates all of the features of interest on object or objects to be inspected while, at the same time, masking or eliminating all of the unwanted features.

Modifications and substitutions by one of ordinary skill in the art are considered to be within the scope of the present invention which is not to be limited except by the claims which follow.

What is claimed is:

1. A method of inspecting a ball and bumped grid array to highlight desired features while masking unwanted features, said method comprising the steps of:
   a. sequentially illuminating said ball and bumped grid array using first and second illumination apparatuses, said first and second illumination apparatuses selected to illuminate said unwanted features similarly and to illuminate said desired features differently;
   b. capturing a first image of said ball and bumped grid array with an image capture device while said array is illuminated with said first illumination apparatus;
   c. capturing a second image of said ball and bumped grid array with said image capture device while said array is illuminated with said second illumination apparatus; and
   d. processing said first and second images by subtracting second image from said first image to produce a resulting image wherein said unwanted features are eliminated.

2. The method claimed in claim 1 further comprising the step of analyzing the desired features of said resulting image.

3. The method claimed in claim 1, wherein said step of illuminating said ball and bumped grid array with said first illumination apparatus comprises illuminating said array with a low angle ring illumination apparatus.

4. The method claimed in claim 3, wherein said step of illuminating said ball and bumped grid array with said second illumination apparatus comprises illuminating said array with a substantially on-axis illumination apparatus, substantially colinear with said image capture device.

5. The method claimed in claim 3, wherein said step of illuminating said ball and bumped grid array with said second illumination apparatus comprises illuminating said array with a high angle ring illumination apparatus.

6. The method claimed in claim 1, wherein said unwanted features are solder vias.

7. The method claimed in claim 1, wherein said desired features are solder balls.

8. A ball and bumped grid array inspection system comprising:
- a first illumination apparatus for illuminating said ball and bumped grid array;
- a second illumination apparatus for illuminating said ball and bumped grid array said second light source selected to illuminate unwanted features of said ball and bumped grid array similarly to said first illumination apparatus;
- an image capture device for capturing at least first and second images of said ball and bumped gird array, said first image corresponding to said array illuminated by said first illumination apparatus and said second image corresponding to said array illuminated by said second illumination apparatus; and
- an image processor for subtracting said second image from said first image to produce a resulting image substantially devoid of said unwanted features.

9. The ball and bumped grid array inspection system of claim 8, wherein said first illumination apparatus comprises a low angle ring illumination apparatus.

10. The ball and bumped grid array inspection system of claim 8, wherein said second illumination apparatus comprises a substantially on-axis illumination apparatus, substantially colinear with said image capture device.

11. The ball and bumped grid array inspection system of claim 8, wherein said image capture device comprises a charged coupled device (CCD) camera.

12. The ball and bumped grid array inspection system of claim 11, wherein said first and second images of said array comprise grey-scale images.

13. The ball and bumped grid array inspection system of claim 8 further comprising at least a third illumination apparatus for illuminating said ball and bumped grid array, said at least a third illumination apparatus selected to illuminate additional unwanted features of said array in a manner similar to said second illumination apparatus, wherein said image capture device captures a third image of said array when said array is illuminated by said third illumination apparatus and said image processor further subtracts said third image from said resulting image to produce a further resulting image, which is substantially devoid of said additional unwanted features.

14. A method of inspecting an article to highlight desired features while masking unwanted features, said method comprising the steps of:
- a. sequentially illuminating said article using first and second illumination apparatuses, said first and second illumination apparatuses selected to illuminate said unwanted features similarly and to illuminate said desired features differently;
- b. capturing a first image of said article with an image capture device while said article is illuminated with said first illumination apparatus;
- c. capturing a second image of said article with said image capture device while said article is illuminated with said second illumination apparatus; and
- d. processing said first and second images by subtracting said second image from said first image to produce a resulting image wherein said unwanted features are eliminated.

15. The method of claim 14 further comprising the steps of:
- illuminating said article with at least a third illumination apparatus, said at least a third illumination apparatus selected to illuminate additional unwanted features of said article in a manner similar to said second illumination apparatus;
- capturing at least a third image of said article with said image capture device while said article is illuminated with said third illumination apparatus; and
- subtracting said at least a third image from said resulting image using an image processor to produce a further resulting image, which is substantially devoid of said additional unwanted features.

16. The method of claim 14 wherein said article includes a background, and wherein said desired features and said unwanted features are both present on said background.

17. The method of claim 16 wherein said desired features and said unwanted features are both three-dimensional reflective features.

* * * * *